| | | |
|---|---|---|
| United States Patent [19] | [11] | 4,207,263 |
| Hoffmann et al. | [45] | Jun. 10, 1980 |

[54] MANUFACTURE OF SECONDARY AMINES BY ALKYLATING AMMONIA WITH ALCOHOLS

[75] Inventors: Herwig Hoffmann; Herbert Mueller; Herbert Toussaint, all of Frankenthal; Arnold Wittwer, Ludwigshafen, all of Fed. Rep. of Germany

[73] Assignee: BASF Aktiengesellschaft, Fed. Rep. of Germany

[21] Appl. No.: 8,155

[22] Filed: Jan. 31, 1979

Related U.S. Application Data

[63] Continuation of Ser. No. 837,937, Sep. 29, 1977, abandoned.

[30] Foreign Application Priority Data

Oct. 9, 1976 [DE] Fed. Rep. of Germany ....... 2645712

[51] Int. Cl.$^2$ ............................................. C07C 85/06
[52] U.S. Cl. ........................... 260/583 R; 260/563 R; 260/581; 260/585 B
[58] Field of Search ........................ 260/585 B, 583 R

[56] References Cited

U.S. PATENT DOCUMENTS

| | | | |
|---|---|---|---|
| 2,065,113 | 12/1936 | Bottoms | 260/585 A X |
| 3,223,734 | 12/1965 | Fallstad et al. | 260/583 R |
| 3,520,933 | 7/1970 | Adam et al. | 260/585 B |
| 3,803,137 | 4/1974 | Egan et al. | 260/585 B X |

FOREIGN PATENT DOCUMENTS

| | | | |
|---|---|---|---|
| 306414 | 5/1930 | United Kingdom | 260/585 B |
| 649980 | 2/1951 | United Kingdom | 260/585 B |
| 679014 | 9/1952 | United Kingdom | 260/585 B |
| 679712 | 9/1952 | United Kingdom | 260/585 B |
| 679713 | 9/1952 | United Kingdom | 260/585 B |
| 1077949 | 8/1967 | United Kingdom | 260/585 B |
| 1451777 | 10/1976 | United Kingdom | 260/585 B |

*Primary Examiner*—John Doll
*Attorney, Agent, or Firm*—Keil & Witherspoon

[57] ABSTRACT

A process for the manufacture of secondary amines, especially fatty amines, from alcohols and ammonia over a hydrogenating catalyst in the presence of hydrogen, in which the reaction mixture essentially consists of alcohol and the amine formed, with only little ammonia, the latter being added progressively and the water formed in the reaction being removed progressively.

12 Claims, No Drawings

MANUFACTURE OF SECONDARY AMINES BY ALKYLATING AMMONIA WITH ALCOHOLS

This is a continuation of application Ser. No. 837,937, filed Sept. 29, 1977, now abandoned.

The present invention relates to a process for the manufacture of secondary amines by alkylating ammonia by means of alcohols, which process can be carried out essentially under atmospheric pressure.

The catalytic alkylation of ammonia by means of alcohols has been disclosed. On the one hand, dehydrating oxides, eg. of aluminum, thorium, tungsten and chromium, are used as catalysts for this reaction, whilst on the other hand hydrogenating or dehydrating catalysts based on copper, nickel, cobalt and noble metals have been recommended. Both liquid phase and gas phase methods have been proposed. A detailed review of this field is given by V. A. Nekrasova and N. I. Shuikin in Russian Chemical Reviews, 34 (1965), 843, by Houben-Weyl, "Methoden der organischen Chemie", 1957, volume 11/1, Nitrogen Compounds 2, page 126, and in German Published Application DAS 2,255,701.

The manufacture of secondary amines by alkylating ammonia by means of alcohols is difficult. This is well-known to be a stepwise reaction which also gives primary and tertiary amines. In addition, mixed amines are formed as by-products and are difficult to isolate in a pure form from the reaction products. Furthermore, a relatively large amount of by-products is formed by dehydrogenation and dehydration of the alcohols and by the resulting secondary reactions.

The manufacture of secondary amines from secondary alcohols and ammonia is particularly difficult. German Laid-Open Application DOS 1,439,781 describes in detail the aminolysis of secondary alcohols with ammonia over hydrogenating/dehydrogenating catalysts under atmospheric pressure. Under comparable conditions, the reaction of 1-octanol and 2-octanol with ammonia gives, respectively, a conversion of 16% of 1-octanol and 72% of 2-octanol. This result, which is unsatisfactory even in the case of 2-octanol, is only achieved if, in accordance with the conditions specified in the DOS, at least the stoichiometric amount of ammonia is reacted with the alcohol. Accordingly, the ammonia must be present in the reaction zone in an amount at least equimolar to the amount of alcohol, ie. an excess of alcohol in the reaction mixture interferes with the uniform course of the reaction.

U.S. Pat. No. 3,223,734 discloses processes for the manufacture of tertiary amines, inter alia from ammonia and an alcohol. In a first stage, ammonia is reacted with the alcohol under normal pressure below 150° C. in the presence of a hydrogenating/dehydrogenating catalyst. This reaction is very non-specific so that at this stage a mixture of primary amine, tertiary amine and, inter alia, 22% of secondary amine is obtained.

An improved process for the manufacture of secondary amines is disclosed in German Published Application DAS 2,255,701. Primary alcohols are reacted with ammonia in the liquid phase over a suspended hydrogenating/dehydrogenating catalyst, and the DAS recommends adhering to defined ammonia/hydrogen gas velocities, under normal pressure or slightly superatmospheric pressure, and preferably above 160° C. The gases, available in excess, at the same time serve to remove the resulting water of the reaction from the reaction mixture. The ammonia available in excess is intended to repress the formation of tertiary amines, in accordance with the rules of physical chemistry; a comparison in fact shows that if a low amount of ammonia is available, triisooctylamine is formed in a yield of 65% from isooctanol. In contrast, if an excess of ammonia is available, 85% of diisooctylamine is formed. The method described evidently entails substantial expenditure on equipment, and requires careful monitoring—for example, care must always be taken not to have less than a minimum amount of ammonia present, since the proportion of tertiary amine otherwise rises. On the other hand the process is carried out—particularly in the final stage of the reaction—at a high temperature, namely at from 190° to 200° C. This on the one hand again favors the formation of tertiary amines and, on the other hand, favors the formation of by-products, for example nitriles and hydrocarbons. In the event of a disturbance, the side reactions and secondary reactions may even predominate.

It is an object of the present invention to provide an improved process for the manufacture of secondary amines from ammonia and alcohols which process gives better selectivity in respect of the formation of secondary amines than conventional processes, and provides virtually complete conversion of the alcohols, since isolating the alcohols by distillation is uneconomical. Another object is to repress, as far as possible, the formation of residues and condensation products of higher molecular weight, since these eventually make the catalyst unusable and can, in many cases, not be removed. It is a further object of the invention to provide a process which can be carried out at a lower and hence more advantageous temperature and in simple equipment, which process for example does not require gas recirculation and which takes place without the presence of hydrogen, especially under atmospheric pressure. Finally, it is an object of the present invention to provide a new process particularly suitable for the manufacture of secondary amines from secondary alcohols (we draw attention to the fact that the word "secondary" has different meanings when applied to alcohols and to amines).

We have found that these objects are achieved and that secondary amines are obtained, under conditions which substantially avoid the above disadvantages, by reacting substantially stoichiometric amounts of ammonia with a primary or secondary alcohol over a catalyst which possesses hydrogenating/dehydrogenating properties, in the presence or absence of hydrogen and of inorganic bases, if at least the first half, preferably at least 80%, and particularly at least 90%, of the ammonia is fed to the liquid reaction mixture, containing the particular alcohol, at the rate at which the reaction proceeds, and water is removed at the rate at which it is formed.

Accordingly, the general concept of the invention is that the reactants, ie. the alcohol and the ammonia, are brought together in a manner which ensures that the reaction mixture is very deficient in ammonia. The alcohol or—in batchwise operation—a reaction mixture which contains the alcohol and more and more reaction product, essentially forms the liquid phase. Accordingly, the latter contains a large molar excess of the alcohol—at least at the beginning of the reaction—and at the same time contains the hydrogenating/dehydrogenating catalyst, which is advantageously additionally activated by the presence of an inorganic base. At equilibrium at any given time, the ammonia should preferably not exceed 5% by weight based on the reaction mixture. The requirements with respect to ammonia feed velocity obviously depend on the desired product quality.

To achieve the said conditions, the simplest procedure is to supply the ammonia in the gaseous form to the liquid reaction mixture, advantageously starting from a reaction mixture which does not contain any ammonia and which is already approximately at a temperature which ensures that the reaction commences immediately. In the course of the reaction, the ammonia concentration should preferably not exceed 5%.

Of course it is also possible to add liquid ammonia, for example by means of a metering device, and this process is advisable when the reaction temperature (under isobaric reaction conditions) is so high that a fairly high concentration of ammonia cannot build up in the reaction mixture. Evidently, this method of operation will also not cause any substantial amount of ammonia, let alone an excess, to be present.

The above comments mean that in batchwise operation the reaction is carried out with gradual addition of ammonia until the alcohol has been consumed, and that the desired amine can be isolated from the liquid reaction mixture by distillation. Small amounts of unreacted alcohol and of primary amine formed can be separated off as first runnings and be re-used for the synthesis of the secondary amine. In this way it proves possible, in most cases, to produce the secondary amine with virtually quantitative selectivity. Similarly, in continuous operation the ammonia, for example in the form of a gas, travels in counter-current to, or in the same direction as, the liquid reaction mixture containing the alcohol (with or without secondary amine), and, if necessary or desired, a post-reaction zone may be provided.

A further essential characteristic of the invention is that the water of reaction formed is always removed continuously from the reaction mixture; this means that, in general, reaction conditions under which water automatically leaves the reaction mixture are employed.

The following picture may help in understanding the invention: if the reaction takes place in the gas phase, it is necessary to choose a very high reaction temperature since many alcohols, above all industrially important alcohols, are of relatively low volatility. This results in a low yield and in impure products. If, on the other hand, the process is carried out in the conventional manner in the liquid phase with the conventional catalysts, in particular catalysts which have not been activated by inorganic bases, it is necessary to use temperatures above 160° C. in order to achieve sufficiently high conversion, so that the reaction becomes substantially non-specific.

The amount of water, which also increases with increasing conversion, is also detrimental. Presumably, it interferes with the activating effect of the bases. In principle the process of the invention may also be carried out without added bases, if care is taken to avoid excessively high temperatures and if some increase in the reaction time can be tolerated.

Accordingly, if the synthesis is to succeed with high yields and above all with a high rate of reaction under mild conditions, the presence of, for example, from 0.01 to 10, preferably from 0.01 to 5, % by weight, based on the hydrogenating/dehydrogenating catalysts, of a base which is derived from an alkali metal or alkaline earth metal is important. For example, the following may be used: sodium hydroxide, lithium hydroxide, potassium hydroxide, sodium carbonate, sodium bicarbonate, calcium hydroxide and calcium oxide. Of course, several of the said compounds may be present simultaneously during the reaction. The use of alkali metal carbonates is preferred. The bases may be used in the solid form, as powders, or in the form of, for example, concentrated solutions, together with the hydrogenating/dehydrogenating catalyst. Preferably, the bases are added in the solid form. As stated, the presence of the bases activates the catalysts and makes it possible to lower the reaction temperature and/or to raise the rate of reaction. In turn, this results in the reactions taking place very selectively. As a result of being able to lower the reaction temperature by about 50° C. compared to the conventional reaction temperature range, it proves possible to limit the extent of side-reactions and the formation of tertiary amines. The formation of small amounts of the primary amine is not detrimental to the process, since this primary amine can be isolated and reacted with further alcohol to give the desired secondary amine.

Though the reaction can be carried out in the absence of hydrogen—according to the empirical equation, hydrogen itself does not participate in the reaction—it has in some cases proved advantageous to have a small amount of hydrogen present in the reaction chamber. In most cases, however, the presence of hydrogen is dispensed with, if only for economic reasons. Alkali-treated catalysts are advantageous, especially if no hydrogen is present.

In principle, all conventional hydrogenating/dehydrogenating catalysts may be used to carry out the reaction according to the invention. However, particularly good results are obtained with nickel catalysts. Amongst these, Raney nickel, nickel on an alumina carrier, nickel on pumice, nickel on kieselguhr and nickel on magnesium oxide may be mentioned. Useful results are also obtained with catalysts based on chromium and copper. Whilst the conventional noble metal catalysts, for example those based on platinum and palladium, are suitable, they are in most cases not used, since they exhibit no advantages. The catalysts—especially the nickel-containing catalysts—are employed in catalytically active amounts of, for example, from 1 to 100%, preferably from 5 to 40%, based on the amount of alcohol originally present. The catalysts can very frequently be reused. For this reason, the use of larger amounts or higher concentrations, for example the use of concentrated suspensions of the catalyst in the reaction mixture, is entirely economical.

The alcohols which can be reacted with ammonia in accordance with the process of the invention include primary and secondary alcohols of all kinds. The best results are obtained with alcohols which are of 4 or more carbon atoms; there is no upper limit to the number of carbon atoms. Commercially important alcohols, in the context of the invention, are of, for example, 4 to 25 carbon atoms.

Products obtainable according to the invention which are industrially particularly important are the di-fatty alkylamines. They are derived from alcohols of up to 22 carbon atoms (fatty alcohols). Examples include n-octanol, isooctanol, n-decyl alcohol, isodecyl alcohol, tridecyl alcohol, stearyl alcohol, cyclooctanol, octanol and heptanol-3 and their mixtures, and the amines which may be manufactured from these.

The reaction proceeds with good yields at 60° to 170° C. The preferred temperatures are from 100° to 150° C.

The reaction may be carried out under superatmospheric or atmospheric pressure, depending on the molecular weight of the alcohol and on the chosen reaction temperature. Pressures below 2 bars are preferred. Occasionally the reaction may be carried out under reduced pressure. Advantageously, the process is carried out under constant pressure, for example at the boil of the reaction mixture, which permits easy control of the course of the reaction.

If a high-boiling alcohol, for example hexanol or octanol, is used to alkylate ammonia, it suffices to heat the alcohol and to introduce ammonia, in the presence of the catalyst, at the rate at which it reacts. The water formed in the reaction is distilled continuously from the reaction system. This removal of water can be assisted by employing a suitable solvent (ie. entraining agent), eg. an aliphatic or aromatic hydrocarbon, to remove the water of reaction, for example as an azeotrope, the water then being separated from the solvent.

A suitable reaction chamber is, for example, a reactor equipped with a stirrer, a condenser and a water separator. In a particularly simple method, ammonia, with or without hydrogen, is bubbled as a gas through the alcohol which has been brought to the reaction temperature. At the same time, the water formed is removed as water vapor from the reaction zone and is then condensed, and small amounts of unconsumed gas may, if desired, be recycled.

In a particularly advantageous method, which also gives the best results, an amount of ammonia equal to that converted per unit time is fed to the alcohol per unit time. The conversion can be measured by determining the amount of off-gas. Depending on the amount of catalyst, it is possible to introduce, for example, from 0.05 to 0.5, preferably 0.1 to 0.5, mole of ammonia per hour into the reaction mixture per mole of alcohol. The amount of hydrogen to be used may be of the same order of magnitude but can be varied within wide limits. It will be seen from the above that it is advantageous to choose reaction conditions under which the conversion requires from about 1 to 10 hours, though shorter or longer reaction times are entirely feasible. In addition, the rate of reaction is of course determined by the amount of ammonia added per unit time; there appears to be no lower limit to this amount.

An aspect of the present invention which can be singled out particularly is that the reaction can be carried out at lower temperatures than has generally been considered feasible for the alkylation of ammonia by means of alcohols. For example, temperatures down to 100° C. can readily be used for the reaction according to the invention. The upper temperature limit at which the reaction can still be carried out with high selectivity is in general above 170° C.; in many cases a satisfactory selectivity is achievable even above this temperature. Temperatures from 100° to 150° C. are preferred.

Since it is, inter alia, an object of the process according to the invention to convert the alcohol as completely as possible, the total amount of ammonia made available over the course of the reaction time is at least equal to the stoichiometric amount. In most cases, in order to avoid unduly long reaction periods, a slight excess of ammonia over the unreacted alcohol becomes necessary toward the end of the reaction, ie., after a conversion of 80, especially 90%, has been attained. This excess may average from 1 to 50 mole %, preferably from 5 to 20 mole%, over the residual alcohol, ie. where necessary the reaction conditions are maintained until an appropriate conversion may be expected. In any case, the ammonia consumption should be at least 50% of the stoichiometric amount before the reaction conditions are changed. In some cases it has proved advantageous to add small amounts of hydrogen, for example from 5 to 10%, to the ammonia in the final stage.

It is essential that the ammonia is added, for most of the reaction time, at the rate at which it is converted. The result of this is, according to the invention, that the ammonia always encounters an excess of alcohol, at least as long as there remains a significant concentration of alcohol in the reaction mixture. These conditions are very easy to achieve by, for example, using a countercurrent method, which can furthermore advantageously be carried out continuously.

In the Examples which follow, amounts are by weight and parts bear the same relation to parts per volume as that of the kilogram to the liter.

EXAMPLE 1

1,080 parts of stearyl alcohol, 300 parts of Raney nickel and 10 parts of sodium carbonate are introduced under atmospheric pressure into a stirred apparatus fitted with a dephlegmator which is kept at 100° C. The reaction mixture is heated, ultimately to 140° C. When the mixture has reached 90° C., ammonia is passed in at the rate at which it is consumed. The alkylation reaction commences at from 90° to 100° C., as may be seen from the elimination of water. The water vapors are condensed in a condenser downstream from the dephlegmator. The amount condensed can be determined and used as a measure of the conversion. When the reaction temperature has been reached, about 14 parts of ammonia per hour are fed into the reaction mixture. After 5 hours the elimination of water has slowed down greatly and the reaction is discontinued. At that point, about 90% of the theoretical amount of water has been obtained. The reaction mixture is cooled and filtered at from 90° to 100° C. The reaction product is fractionated by distillation. At from 140° to 150° C. under 0.3 mbar, about 20 mole%, based on the alcohol employed, of first runnings consisting of 80% of monostearylamine and 20% of stearyl alcohol are obtained. About 80 mole%, based on the alcohol employed, remain as a colorless distillation residue. This residue contains more than 95% of distearylamine, and its amine number is 103 [mg KOH/g]; the theoretical amine number is 108. The tristearylamine content is less than 3%. The first runnings obtained can be re-used for the manufacture of distearylamine and are therefore a useful product. If this secondary yield is taken into account, the selectivity is over 95%, which in a continuous process would be about the total achievable yield.

Similar results are obtained if potassium carbonate is used as the catalyst additive. If sodium bicarbonate or potassium bicarbonate are employed as the catalyst additive in the reaction, the rate of reaction is found to be increased by about a further 20%.

The same result as with sodium carbonate is obtained if 10 parts of calcium oxide, 10 parts of calcium hydroxide or 10 parts of barium hydroxide are added. If 0.5 part of powdered sodium hydroxide is added, the rate of reaction is found to be from 40 to 50% lower, but this is still about 30% higher than in an experiment in the absence of bases.

If the Raney nickel is replaced by an equal amount of Raney cobalt and the reaction is carried out at 155° C., a selective reaction is in principle again achievable.

However, a reaction time of 8 hours is required for 30% conversion.

EXAMPLE 2

The procedure described in Example 1 is followed. 650 parts of 2-ethyl-hexan-1-ol, 300 parts of a reduced nickel catalyst which contains 60% of nickel on kieselguhr and 7 parts of sodium bicarbonate are heated to 140° C. and at this temperature ammonia gas is passed into the well-stirred suspension at the rate at which it is converted. The reaction ends after 8 hours. The mixture is worked up by distillation and gives 96% of theory of di-2-ethylhexylamine, 1% of theory of 2-ethylhexylamine and 0.3% of theory of tri-2-ethylhexylamine.

EXAMPLE 3

The procedure described in Example 1 is followed. 700 parts of cyclohexanol, 300 parts of Raney nickel and 10 parts of sodium carbonate are treated with ammonia for 4 hours at 140° C. After filtration, the reaction product is distilled. No distillation residue is found. The distillate consists of a mixture of 92% of dicyclohexylamine, 3% of monocyclohexylamine and 3% of tricyclohexylamine together with 2% of unconverted alcohol.

If heptan-3-ol is reacted similarly with ammonia at 130° C., 80% of theory of di-3-heptylamine, 18.5% of theory of 3-heptylamine and 0.5% of theory of unconverted alcohol are obtained.

EXAMPLE 4

The procedure described in Example 1 is followed. 744 parts of n-dodecanol, 400 parts of Raney nickel and 10 parts of sodium carbonate are reacted with ammonia. During the reaction, the stoichiometrically calculated amount of water is formed. Distillation of the reaction mixtures gives—calculated as monolaurylamine and based on the alcohol—20 mole% of first runnings consisting of 90% of monolaurylamine and 10% of lauryl alcohol. These first runnings boil at from 95° to 105° C. under 0.3 mbar. The residue which remains consists of 74 mole%, based on alcohol converted, of dilaurylamine containing about 6 mole% of trilaurylamine.

EXAMPLE 5

As an example of a continuous process, a vertical reaction tube is filled with 2,000 parts by volume of a magnesium silicate-supported catalyst which has beforehand been impregnated with concentrated sodium carbonate solution. According to analysis, the catalyst consists of 55% of nickel oxide, 16% of magnesium oxide, 23% of $SiO_2$, 1% of $Cr_2O_3$ and 5% of $Na_2CO_3$; it is in the form of cylindrical moldings having a diameter of 3 mm and a height of 3 mm. The diameter: length ratio of the reaction tube is 1:20. Before starting the reaction, the catalyst is dried and activated by heating at 350° to 400° C. in a stream of hydrogen. The reaction tube, at 140° C., is fed at the top with 200 parts by weight, per hour, of n-dodecan-1-ol. Gaseous ammonia—about 19 parts per hour—is fed into the lower part of the reaction tube. Unconverted ammonia, which escapes at the top of the reaction tube, can be returned to the reaction tube, by means of a gas circulation pump, after it has been freed from the water vapor which it contains. this small amount of ammonia is immaterial as regards the result of the synthesis.

At the bottom of the reaction tube, from 175 to 180 parts by weight of the reaction product can be taken off per hour; the product contains about 85% of dilaurylamine, 8% of monolaurylamine, 3% of n-dodecanol and 4% of trilaurylamine.

We claim:

1. A process for the manufacture of a secondary amine which comprises reacting essentially stoichiometric amounts of ammonia with a primary or secondary monohydric or polyhydric alcohol over a hydrogenating/dehydrogenating catalyst in the presence or absence of hydrogen and in the presence of an inorganic base at a temperature of from 100° to 150° C., wherein at least the first half of the ammonia is fed to the liquid reaction mixture containing the alcohol at the rate at which it reacts, and wherein water is removed at the rate at which it is formed, whereby the added ammonia encounters an excess of alcohol in the reaction mixture until the reaction is substantially complete.

2. A process as in claim 1, in which the reaction is carried out in the presence of a basic alkali metal compound or alkaline earth metal compound.

3. A process as in claim 1 wherein the inorganic base is selected from the group consisting of sodium hydroxide, lithium hydroxide, potassium hydroxide, sodium carbonate, sodium bicarbonate, calcium hydroxide and calcium oxide.

4. A process as in claim 1 wherein the inorganic base is sodium carbonate.

5. A process as in claim 1 in which ammonia is fed in vapor form.

6. A process as in claim 1 in which ammonia is fed to the reaction mixture at a temperature near the boiling point of said mixture and the reaction is allowed to take place under constant pressure.

7. A process as in claim 1 in which the reaction is carried out batchwise until the alcohol is consumed, the secondary amine is isolated from the liquid reaction mixture by distillation and any primary amine obtained is again reacted with the alcohol.

8. A process as in claim 1 in which the reaction is carried out continuously, gaseous ammonia is fed to the liquid reaction mixture containing alcohol, with or without amines, in counter-current to or in the same direction of flow as the reaction mixture, with or without the provision of a post-reaction zone.

9. A process as in claim 1 in which Raney nickel is used as the catalyst.

10. A process as in claim 1 in which the equilibrium amount of ammonia present in the reaction mixture at any time is kept below 5% by weight.

11. A process as in claim 1 in which the alcohol is an alcohol of four or more carbon atoms which behaves as a fatty alcohol.

12. A process as in claim 1 in which an excess of ammonia of from 1 to 50 mole% with respect to unreacted alcohol is added after a conversion of at least 80% has been attained.

* * * * *